United States Patent
Fraser et al.

(10) Patent No.: US 7,045,102 B2
(45) Date of Patent: May 16, 2006

(54) FLUID TREATMENT SYSTEM

(75) Inventors: Jim Fraser, St. Thomas (CA); Wesley From, London (CA); Steven Bakker, London (CA)

(73) Assignee: Trojan Technologies Inc., (CA)

( * ) Notice: Subject to any disclaimer, the term of this patent is extended or adjusted under 35 U.S.C. 154(b) by 52 days.

(21) Appl. No.: 10/678,637

(22) Filed: Oct. 6, 2003

(65) Prior Publication Data

US 2004/0118786 A1 Jun. 24, 2004

Related U.S. Application Data

(60) Provisional application No. 60/416,958, filed on Oct. 9, 2002.

(51) Int. Cl.
*B01J 19/08* (2006.01)
*C02F 1/32* (2006.01)

(52) U.S. Cl. .................... 422/186.3; 210/748; 250/435

(58) Field of Classification Search ................ 210/748, 210/198.1; 422/24, 186.3; 250/432 R, 435, 250/436
See application file for complete search history.

(56) References Cited

U.S. PATENT DOCUMENTS

| | | | |
|---|---|---|---|
| 2,648,774 A | * | 8/1953 | Whitlock ..................... 250/435 |
| 3,672,823 A | * | 6/1972 | Boucher ...................... 422/20 |
| 4,179,616 A | * | 12/1979 | Coviello et al. ......... 422/186.3 |
| 4,367,410 A | | 1/1983 | Wood |
| 4,482,809 A | | 11/1984 | Maarschalkerweerd |
| 4,602,162 A | * | 7/1986 | Sperry et al. ............... 250/436 |
| 4,767,932 A | * | 8/1988 | Ellner ......................... 250/435 |
| 4,872,980 A | | 10/1989 | Maarschalkerweerd |
| 5,006,224 A | | 4/1991 | Smegal et al. |
| 5,200,156 A | * | 4/1993 | Wedekamp ............... 422/186.3 |
| 5,208,461 A | | 5/1993 | Tipton |
| 5,227,140 A | * | 7/1993 | Hager et al. ............. 422/186.3 |
| 5,352,359 A | * | 10/1994 | Nagai et al. ................. 210/192 |
| 5,372,781 A | * | 12/1994 | Hallett et al. ............ 422/186.3 |
| 5,504,335 A | * | 4/1996 | Maarschalkerweerd ..... 250/435 |
| 5,505,912 A | | 4/1996 | Hallett |
| 5,832,361 A | | 11/1998 | Foret |
| 5,885,449 A | * | 3/1999 | Bergmann et al. ........ 210/198.1 |
| 5,937,266 A | | 8/1999 | Kadoya |
| 6,001,247 A | * | 12/1999 | Schulz ....................... 210/192 |

(Continued)

FOREIGN PATENT DOCUMENTS

DE       297 04 749 U       10/1997

(Continued)

*Primary Examiner*—Frank M. Lawrence
(74) *Attorney, Agent, or Firm*—Katten Muchin Rosenman LLP

(57) ABSTRACT

A fluid treatment system for placement in a flanged pipe fluid conveyance system includes: a first flanged opening and a second flanged opening in substantial alignment to define a flow axis aligned substantially parallel to a direction of fluid flow though the first opening and the second opening; and a third flanged opening comprising a first cover element. The first cover element has connected thereto at least one radiation source assembly comprising at least one elongate radiation source having a longitudinal axis substantially transverse to the flow axis. The fluid treatment system may be advantageously utilized to treat fluid such as water, e.g., municipal waste water, municipal drinking water and the like. The fluid treatment system can be readily "spliced" into existing into existing piping systems. This facilitates installation of the system and also allows for a significant lowering of manufacturing costs of the system.

71 Claims, 5 Drawing Sheets

U.S. PATENT DOCUMENTS

| | | | |
|---|---|---|---|
| RE36,896 E * | 10/2000 | Maarschalkerweerd | 422/186.3 |
| 6,402,964 B1 * | 6/2002 | Schmid | 210/748 |
| 6,459,087 B1 * | 10/2002 | Kaas | 250/372 |
| 6,500,346 B1 * | 12/2002 | Taghipour et al. | 210/748 |
| 6,642,527 B1 * | 11/2003 | Wedekamp | 250/436 |
| 6,752,971 B1 * | 6/2004 | Boehme | 422/186.3 |
| 2002/0043504 A1 * | 4/2002 | Chen et al. | 210/748 |
| 2003/0010927 A1 * | 1/2003 | Wedekamp | 250/436 |
| 2003/0129105 A1 * | 7/2003 | Boehme | 422/186.3 |

FOREIGN PATENT DOCUMENTS

| | | |
|---|---|---|
| EP | 0 743 105 A | 11/1996 |
| GB | 1 584 385 A | 2/1981 |
| WO | WO 01/25154 A1 * | 4/2001 |

* cited by examiner

FLUID TREATMENT SYSTEM

CROSS-REFERENCE TO RELATED APPLICATION

The present application claims the benefit under 35 U.S.C. §119(e) of provisional patent application Ser. No. 60/416,958, filed Oct. 9, 2002, the contents of which are hereby incorporated by reference.

BACKGROUND OF THE INVENTION

1. Field of the Invention

In one of its aspects, the present invention relates to a fluid treatment system for placement in a flanged pipe fluid conveyance system. In another of its aspects, the present invention relates to a method of installing a fluid treatment system in an existing piped fluid conveyance system.

2. Description of the Prior Art

Fluid treatment devices and systems are known. For example, U.S. Pat. Nos. 4,482,809, 4,872,980, 5,006,244 and Re.36,896 (all assigned to the assignee of the present invention) all describe gravity fed fluid treatment systems which employ ultraviolet (UV) radiation to inactivate microorganisms present in the fluid.

The devices and systems described in the '809, '980 and '244 patents generally include several UV lamps, each of which are mounted within sleeves extending between two support arms of the frames. The frames are immersed in the fluid to be treated which is then irradiated as required. The amount of radiation to which the fluid is exposed is determined by the proximity of the fluid to the lamps. One or more UV sensors may be employed to monitor the UV radiation output of the lamps and the fluid level is typically controlled, to some extent, downstream of the treatment device by means of level gates or the like. Since, at higher flow rates, accurate fluid level control is difficult to achieve in gravity fed systems, fluctuations in fluid level are inevitable. Such fluctuations could lead to non-uniform irradiation in the treated fluid.

However, disadvantages exist with the above-described systems. Depending on the quality of the fluid which is being treated, the sleeves surrounding the UV lamps periodically become fouled with foreign materials, inhibiting their ability to transmit UV radiation to the fluid. When fouled, at intervals which may be determined from historical operating data or by the measurements from the UV sensors, the sleeves must be manually cleaned to remove the fouling materials. Regardless of whether the UV lamp frames are employed in an open, channel-like system or a closed system, cleaning of the sleeves is impractical.

In open, channel-like systems, the modules comprising the sleeves are usually removed from the channel and immersed in a separate tank containing a suitable cleaning fluid. In closed systems, the device must be shut down and the sleeves are thereafter cleaned by charging with a suitable cleaning fluid or by removal of the lamps in the manner described for the open, channel-like systems. In either type of system, the operator must accept significant downtime of the system and/or invest significant additional capital to have in place sufficient redundant systems with appropriate control systems to divert the flow of fluid from the systems being cleaned.

The system described in the '896 patent is a significant advance in the art in that it obviates a number of disadvantages deriving from the devices and systems '809, '980 and '244 patents. Unfortunately, the system described in the '896 patent is ideally suited for use in an open, channel-like system and is not readily adaptable to be used in a completely closed system where the flow of fluid is fed under pressure in a pipe.

Closed fluid treatment devices are known—see, for example, U.S. Pat. No. 5,504,335 (assigned to the assignee of the present invention). The '335 patent teaches a closed fluid treatment device comprising a housing for receiving a flow of fluid. The housing comprises a fluid inlet, a fluid outlet, a fluid treatment zone disposed between the fluid inlet and the fluid outlet, and at least one radiation source module disposed in the fluid treatment zone. The fluid inlet, the fluid outlet and the fluid treatment zone are in a collinear relationship with respect to one another. The at least one radiation source module comprises a radiation source sealably connected to a leg which is sealably mounted to the housing. The radiation source is disposed substantially parallel to the flow of fluid. The radiation source module is removable through an aperture provided in the housing intermediate to fluid inlet and the fluid outlet thereby obviating the need to physically remove the device for service of the radiation source.

International Publication Number WO 01/25154 (assigned to the Assignee of the present invention) is another prior art reference which teaches a closed fluid treatment device. Specifically, this reference teaches a closed fluid treatment device comprising a housing for receiving a flow of fluid. The housing comprises a fluid inlet, a fluid outlet, a fluid treatment zone disposed between the fluid inlet and the fluid outlet, and at least one radiation source having a longitudinal axis disposed in the fluid treatment zone substantially transverse to the direction of fluid flow through the housing. The fluid inlet, the fluid outlet and the fluid treatment zone are arranged substantially collinearly with respect to one another. The fluid inlet comprises an opening characterized by two features. First, the opening has a cross-sectional area less than a cross-sectional area of the fluid treatment zone. Second, the opening has a largest diameter substantially parallel to the longitudinal axis of the radiation source disposed in the fluid treatment zone.

While the closed fluid treatment devices taught in U.S. Pat. No. 5,504,335 and in International Publication Number WO 01/25154 represent advances in the art, there is still room for improvement. Specifically, it is conventional in the art to custom build such closed fluid treatment devices, typically from stainless steel. In some cases, this can render the fluid treatment significantly more costly to acquire. It would be highly desirable to have a fluid treatment system capable of being utilized in a conventional pipe fitting. Such a device would result in significantly reducing direct manufacturing costs and, in some installations, allow for the system to be readily installed in existing piping systems.

SUMMARY OF THE INVENTION

It is an object of the present invention to obviate or mitigate at least one of the above-mentioned disadvantages of the prior art.

Accordingly, in one of its aspects, the present invention provides a fluid treatment system for placement in a flanged pipe fluid conveyance system, the fluid treatment system comprising:

a flanged ductile iron pipe fitting comprising:

(a) a first flanged opening and a second flanged opening in substantial alignment to define a flow axis aligned substantially parallel to a direction of fluid flow through the first opening and the second opening; and (b) a third flanged opening comprising a first cover element, the first cover element having connected thereto at least one radiation source assembly comprising at least one elongate radiation source having a longitudinal axis substantially transverse to the flow axis.

In another of its aspects, the present invention provides a method of installing a fluid treatment system in an existing piped fluid conveyance system, the method comprising the steps of:

(i) extracting a section of the pipe from the existing piped fluid conveyance system to define a flanged fluid intake and a flanged fluid feed;

(ii) disposing a flanged ductile iron pipe fitting between the flanged fluid intake and the flanged fluid feed, the flanged pipe ductile iron pipe fitting comprising:

(a) a first flanged opening and a second flanged opening in substantial alignment to define a flow axis aligned substantially parallel to a direction of fluid flow through the first opening and the second opening; and (b) a third flanged opening comprising a first cover element, the first cover element having connected thereto at least one radiation source assembly comprising at least one elongate radiation source having a longitudinal axis substantially transverse to the flow axis;

(iii) connecting the first flanged opening to the flanged fluid intake in a substantially fluid tight manner; and (iv) connecting the second flanged opening to the flanged fluid feed in a substantially fluid tight manner.

In yet another of its aspects, the present invention provides a fluid treatment system for placement in a flanged pipe fluid conveyance system, the fluid treatment system comprising:

a flanged non-metallic pipe fitting comprising:

(a) a first flanged opening and a second flanged opening in substantial alignment to define a flow axis aligned substantially parallel to a direction of fluid flow through the first opening and the second opening; and (b) a third flanged opening comprising a first cover element, the first cover element having connected thereto at least one radiation source assembly comprising at least one elongate radiation source having a longitudinal axis substantially transverse to the flow axis.

Thus, the present inventors have developed a novel fluid treatment system for placement in a flanged piped fluid conveyance system. In its preferred form, the present fluid treatment system may be advantageously utilized to treat fluid such as water, e.g., municipal waste water, municipal drinking water and the like. The present fluid treatment system is particularly advantageous since it utilizes a standard ductile iron pipe fitting and thus, can be readily "spliced" into existing piping systems, often referred to as a pipe gallery. This facilitates installation of the system and also allows for a significant lowering of manufacturing costs of the system.

The present fluid treatment system utilizes a flanged ductile iron pipe fitting in which there is disposed a plurality of radiation source assemblies, each radiation source assembly comprising at least one elongate radiation source having a longitudinal axis substantially transverse to the axis of fluid flow through the flanged ductile iron pipe fitting. The flanged pipe fitting is constructed from a standard ductile iron pipe fitting thereby greatly reducing direct manufacturing costs and facilitating installation of the system in an existing fluid conveyance or piping system.

The flanged ductile iron pipe fitting can take a number of different shapes. For example, the flanged pipe fitting can be T-shaped, cruciform-shaped, Y-shaped and the like.

The longitudinal axis of the radiation source in the fluid treatment system is disposed substantially transverse to the direction flow of fluid through the flanged ductile iron pipe fitting. While the preferred orientation of the radiation source is such that its longitudinal axis is substantially orthogonal to the direction of fluid flow through the flanged ductile iron pipe fitting, it is possible to orient the radiation source such that its longitudinal axis is otherwise angled with respect to the direction of fluid flow through the flanged ductile iron pipe fitting.

Flanged ductile iron pipe fittings are generally known in the art and typically are available as "off the shelf" type products. See the following for more information on flanged ductile iron pipe fittings commercially available from U.S. Pipe. Ductile Iron Flanged Pipe With Threaded Flanges and Flanged Fittings For Water and Other Liquids: Flanged pipe and fittings are typical components in rigid piping systems. Such systems are particularly suited for above ground installation in the following: water filtration plants, sewage disposal plants, wastewater treatment plants, pumping stations and industrial plants. U.S. Pipe gives special attention to such installations through its Customer Service Department. The underground use of the flanged joint is generally not recommended due to the rigidity of the joint. Unequal settlement or other stressing of such piping may result in excessive strain on the flanges or the pipe. Threaded flanged pipes are fabricated by threading plain end pipe, screwing threaded flange(s) on and machine-tightening them. The plain end and the flange are then faced to provide a smooth surface across the end of the pipe and the face of the flange. The Foreword of ANSI/AWWA C115/A21.15 Flanged Ductile-Iron Pipe with Ductile-Iron or Gray-Iron Threaded Flanges lists the required information and the Options which if desired must be specified on the purchase order for flanged pipe, such as size and finished length. See the standard for more details. Unless otherwise specified, U.S. Pipe furnishes flanged pipe with; Ductile Iron Threaded Flanges; Cement mortar lining - standard thickness; Standard asphaltic coating inside and out; Special class 53 wall thickness, pressure class 350 for sizes 60" and 64" Bolt holes aligned per A21.15 Standard. Flanged joint accessories (bolts, nuts and gaskets) can be furnished by U.S. Pipe if so specified. Rubber gaskets, ⅛" thick or U.S. Pipe FLANGE-TYTE® Gaskets (4" through 64 41 size) are recommended for normal water or sewage service. When requesting prices for flanged pipe for carrying chemical solutions, complete information regarding the type of material to be conveyed, composition, concentration, pH. pressure and temperature should be specified. Ductile Iron flanged pipe is furnished in accordance with ANSI/AWWA C115/A21.15. Pipe barrels and flanges have a taper pipe thread (NPT) in accordance with B 1.20.1, with thread diameters adapted to Ductile Iron pipe standard outside diameters. Ductile Iron pipe used for flanging are centrifugally cast in metal molds in sizes 3"–64" and meet all requirements of ANSI/AWWA C151/A21.51 Ductile Iron Pipe, Centrifugally Cast. for Water: Pipe for wastewater service may be furnished in accordance with ASTM 746 Standard Specification for Ductile Iron Gravity Sewer Pipe. Flanges conform to the chemical and physical properties specified for Ductile Iron fittings in ANSI/AWWA C115/A21.10 Ductile-Iron and Gray-Iron Fittings, 3 in, through 48 in. (76 mm through 1,219 mm), For Water and ANSI/AWWA C153/A21.53 Ductile-Iron Compact Fittings. For Water Service. Flanged pipe are furnished in the following maximum lengths: Sizes: 4"–42"–17'6"; Sizes: 3", 48"–64"19'6". U.S. Pipe's Flanged Fittings are produced of Ductile Iron and conform to the applicable requirements for Ductile Iron fittings specified in ANSI/AWWA C110/A21.10 (3-through 48-in, sizes) and ANSI/AWWA C153/A21.53 (54-through 64-in, sizes). The flanges of the C110/A21.10 and C153/A21.53 Standards conform to the drilling and facing of ANSI B16.1 Class 125 flanges. This B16.1 Class 125 designation leads some to conclude that these AWWA flanges are only rated at 125 psi service which is not correct. The C110/A21.10 Standard flanges are rated for 350 psi operating pressure for 12 inch and smaller sizes and 250 psi operating pressure for 14 inch and larger sizes at ambient temperatures with at least a 2:1 factor of safety. Special gaskets such as U.S. Pipe's FLANGE-TYTE® Gaskets are used for operating pressures greater than 250 psi. (Flanges of Ductile Iron pipe and fittings meeting the requirements of ANSI/AWWA C115/A21.15 or ANSI/AWWA C110/A21.10 cannot be joined with Class 250 ANSI B16.1 flanges.) Face-to-face dimensions conform to a tolerance of ±0.12 in. for sizes 3–64 in. Threaded pipe and threaded flanges are individually fitted and the flanges are not interchangeable. The minimum class thickness for Ductile Iron flanged pipe to be threaded is specified in ANSI/AWWA C115/21.15 to be ANSI/AWWA C151/A21.51 class 53 for sizes up through 54 in, and pressure class 350 for 60 and 64 in. sizes. Flanged pipe can be furnished with greater wall thicknesses than special class 53 if so ordered. Weights shown are subject to a minus tolerance of not more than 10% for individual pieces. To obtain the weight of any short length of pipe, calculate the weight of the length from face to face of flanges and add the weight of two flanges. The gaskets and bolts to be used with flanged pipe and fittings should be selected by the purchaser with due consideration for the particular service and installation requirements.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
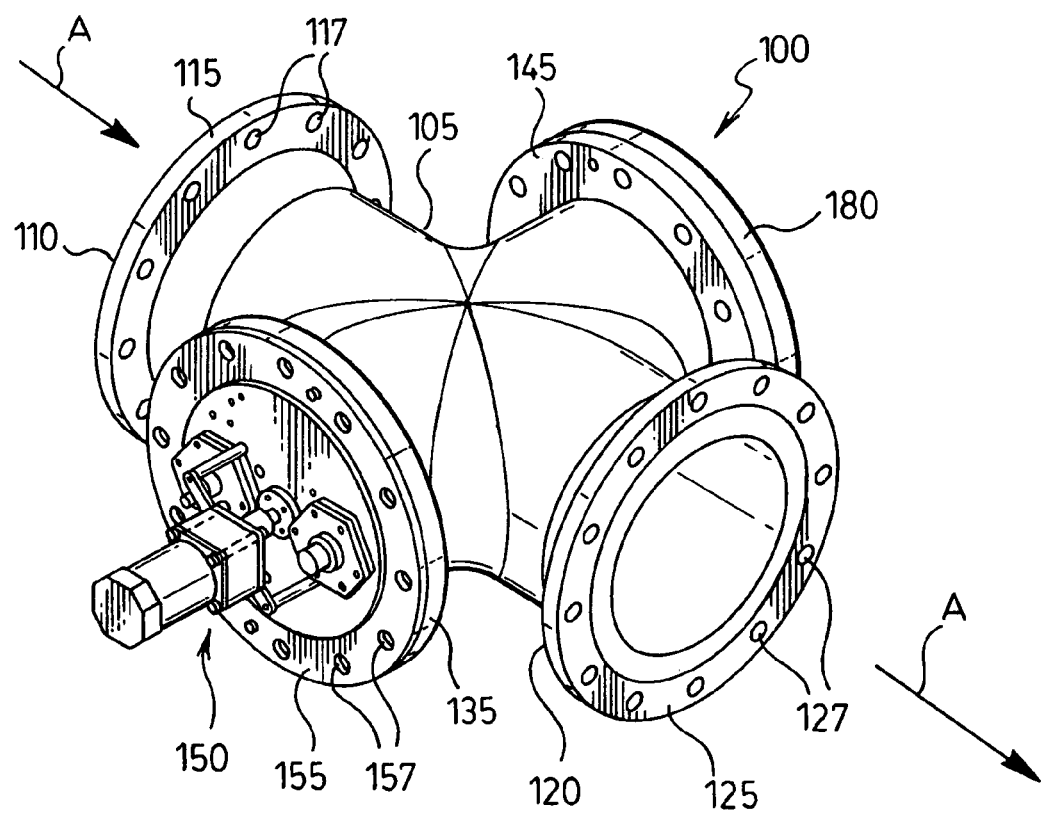
FIG. 1 illustrates a perspective view of a first embodiment of the present fluid treatment system.
Figure 2:
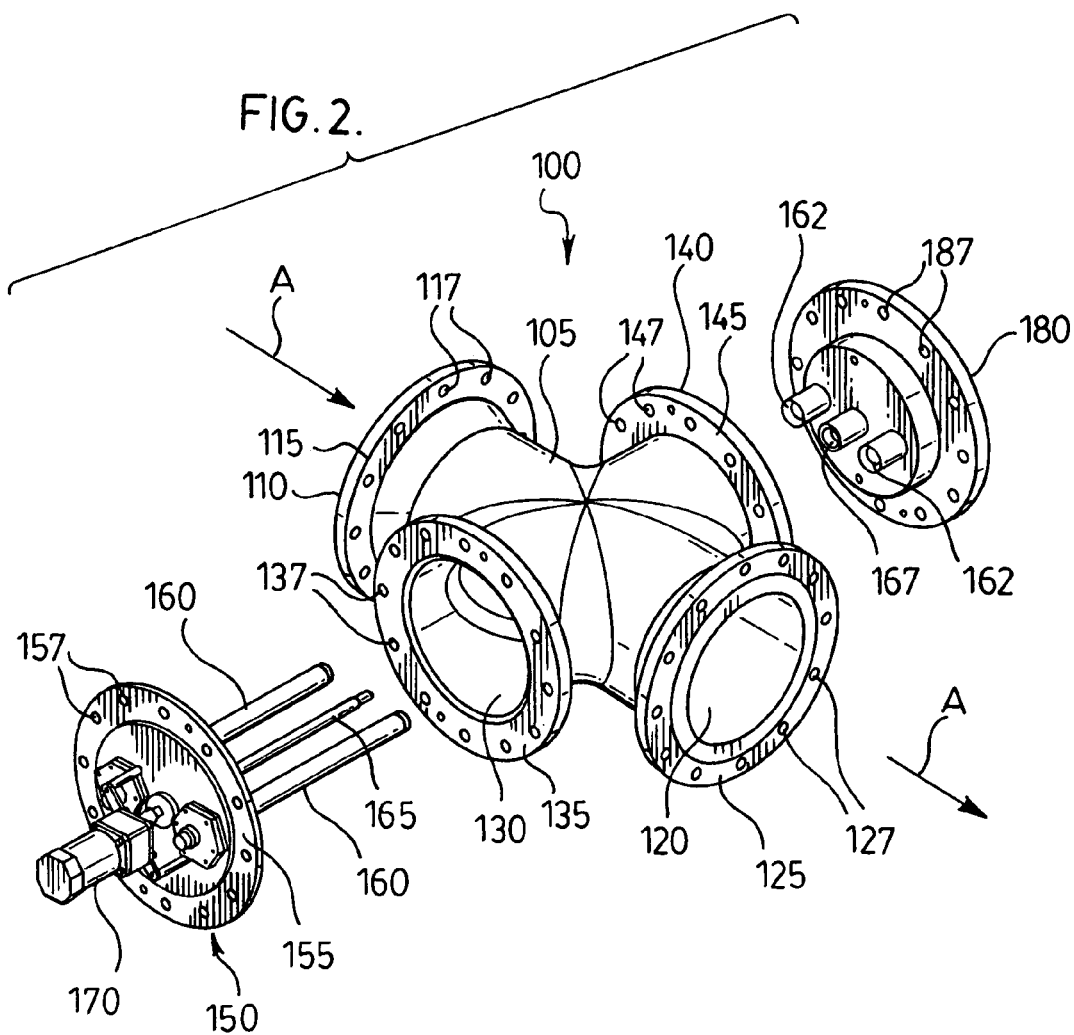
FIG. 2 illustrates the fluid treatment system shown in FIG. 1 in disassembled form.
Figure 3:
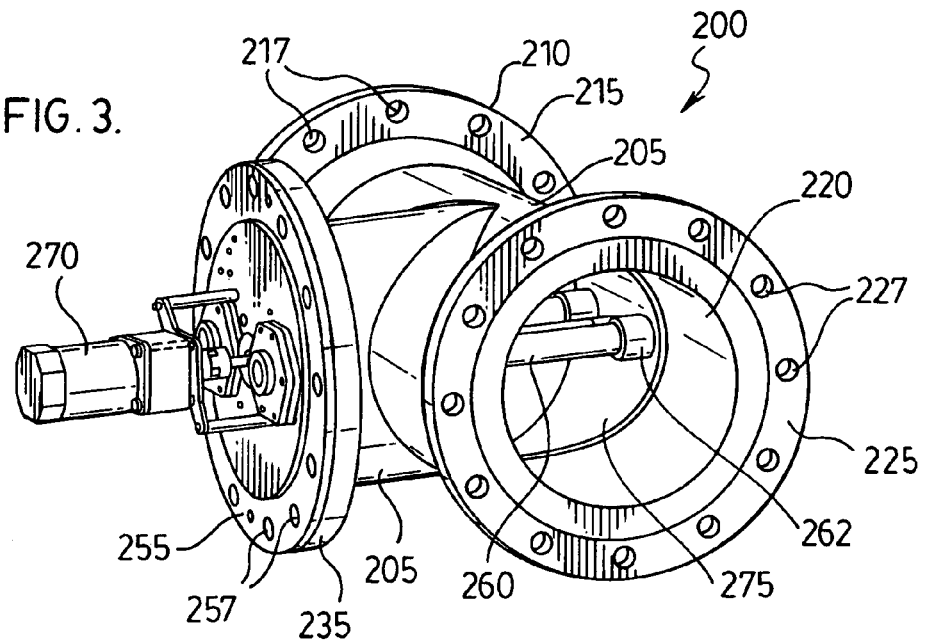
FIG. 3 illustrates a perspective view of a second embodiment of the present fluid treatment system.

With references to FIGS. 1 and 2, there is illustrated a fluid treatment system 100. Fluid treatment 100 comprises a flanged ductile iron pipe fitting 105. Pipe fitting 105 comprises a first flanged opening 110 and a second flanged opening 120. First flanged opening 110 comprises a flange plate 115 having a series of connection openings 117. Second flanged opening 120 comprises a flange plate 125 having a series of connection opening 127.

Pipe fitting 105 further comprises a third flanged opening 130 and a fourth flanged opening 140. Third flanged opening 130 comprises a flange plate 135 and a series of connection openings 137. Fourth flanged opening 140 comprises a flange plate 145 and a series of connection openings 147.

Thus, it will be apparent that flanged openings 110 and 120 are coaxially aligned along the direction of fluid flow depicted by arrow A. Similarly, flanged openings 130 and 140 are coaxially aligned along an axis (not shown for clarity) which is oriented orthoganally with respect to the axis along which flanged openings 110 and 120 are aligned.

Fluid treatment system 100 further comprises an insertable radiation source module 150. Radiation source module 150 comprises a cover plate 155 having a series of connection apertures 157 in substantial alignment with connection openings 137 of third flanged plate 135. Radiation source module 150 further includes a pair of radiation source assemblies 160. Each radiation source assembly comprises a radiation source disposed in a protective sleeve such as quartz (these elements are not shown for clarity). Preferably, the radiation source is an ultraviolet radiation source such as a low pressure ultraviolet radiation lamp, a medium pressure ultraviolet lamp, a low pressure high output ultraviolet radiation lamp, an amalgam ultraviolet radiation lamp and the like.

Radiation source module 150 further comprises a shaft 165 along which a cleaning device (not shown in FIGS. 1 and 2) may be translated back and forth. A motor 170 is disposed on the opposite side of radiation source module cover plate 155 for operating the cleaning device.

Fluid treatment system 100 further comprises a cover plate 180 which comprises a pair of support receptacles 162 for receiving the distal end of radiation source assemblies 160 and support receptacle 167 for receiving the distal end of shaft 165. Cover plate 180 further comprises a series of connection openings 187 in substantial alignment with connection openings 147 in flange plate 145.

Fluid treatment system 100 may be assembled by aligning connection openings 157 and 137, and bolting plate 155 to flange plate 135 in a convention manner. Similarly, cover plate 180 is aligned with flange plate 145 such that support receptacles 162 receive radiation source assemblies 160 and support receptacle 167 receives shaft 165.

Once fluid treatment system 100 is assembled, it may then be installed in an existing fluid conveyance system. Conventional fluid conveyance systems are constructed from materials such as ductile iron pipe fittings, polymer material and the like. Fluid treatment system 100 may be installed by removing a section of an existing fluid conveyance system to produce a flanged fluid intake and a flanged fluid feed (not shown). Flanged plate 115 would then be aligned with the flanged fluid intake, and flange plate 125 would be aligned with the flanged fluid feed. Fluid type connections would be made in a conventional manner and fluid treatment system 100 would then be ready for operation in a conventional manner.

With reference to FIGS. 3–6, there is illustrated a fluid treatment system 200. Generally, fluid treatment system 200 differs from fluid treatment system 100 illustrated in FIGS. 1–2 in that the former utilizes a cruciform-shaped ductile iron pipe fitting whereas the latter utilizes a T-shaped ductile iron pipe fitting.

Fluid treatment system comprises a first flanged opening 210. First flanged opening 210 comprises a flange plate 215 having a series of connection openings 217 disposed therein. Fluid treatment system 200 further comprises a second flanged opening 220. Second flanged opening 220 comprises a flange plate 225 having a series of connection openings 227 disposed therein. Ductile pipe fitting 205 or the like (e.g., a pipe fitted constructed from an alternate material such as polymers, plastics, fibre-glass, composites of these and the like) further comprises a third flanged opening 230. Third flanged opening 230 comprises a flange plate 235 comprising a series of connection openings 237.

Figure 4:
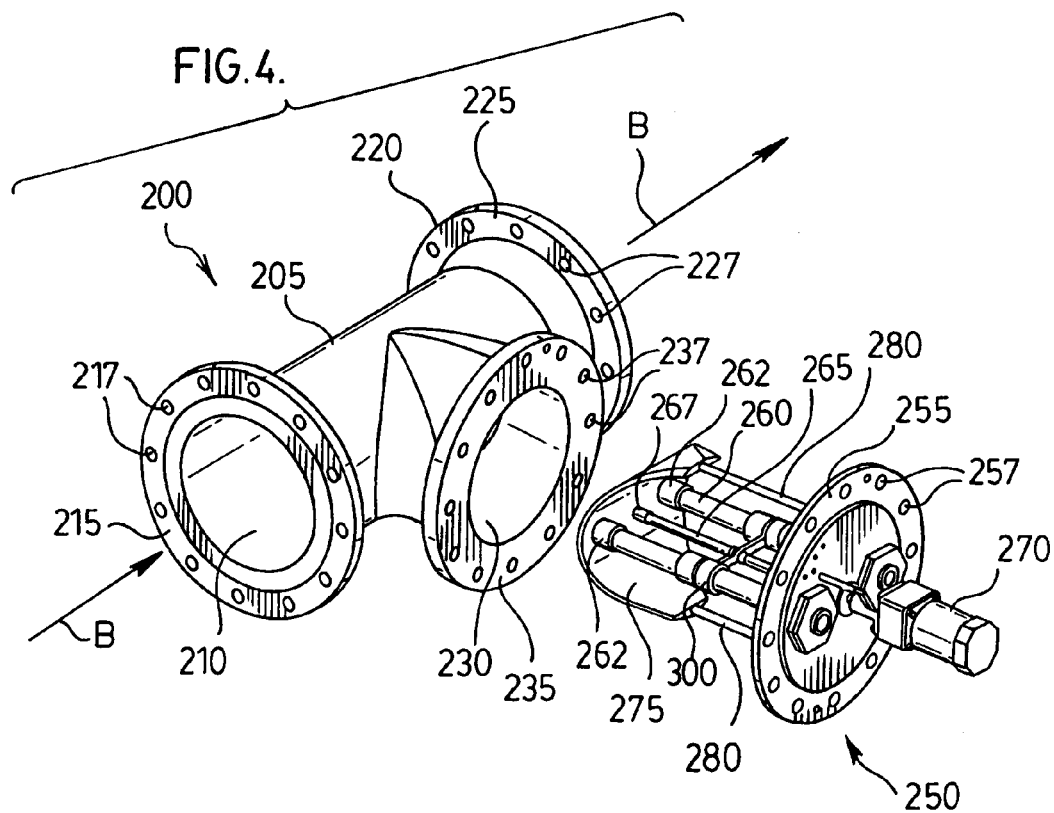
FIGS. 4–6 illustrate the fluid treatment system shown in FIG. 3 in disassembled form.
Figure 5:
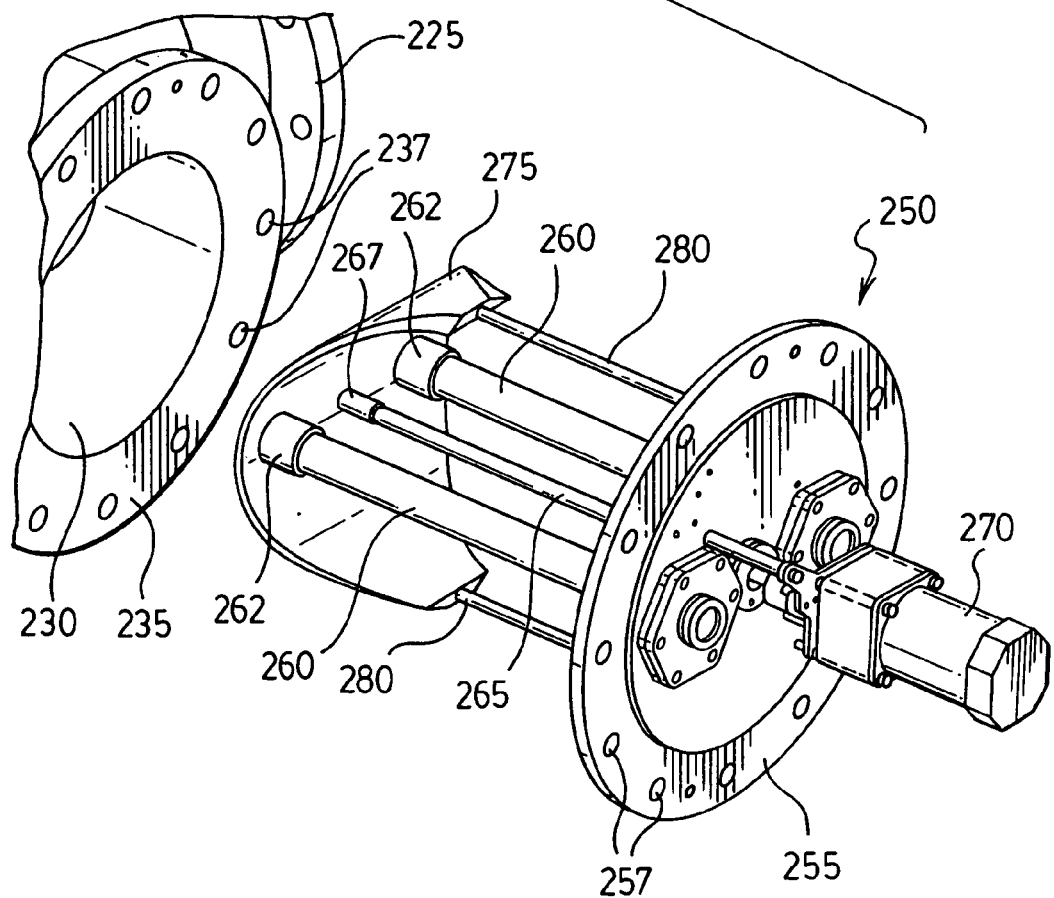
Figure 6:
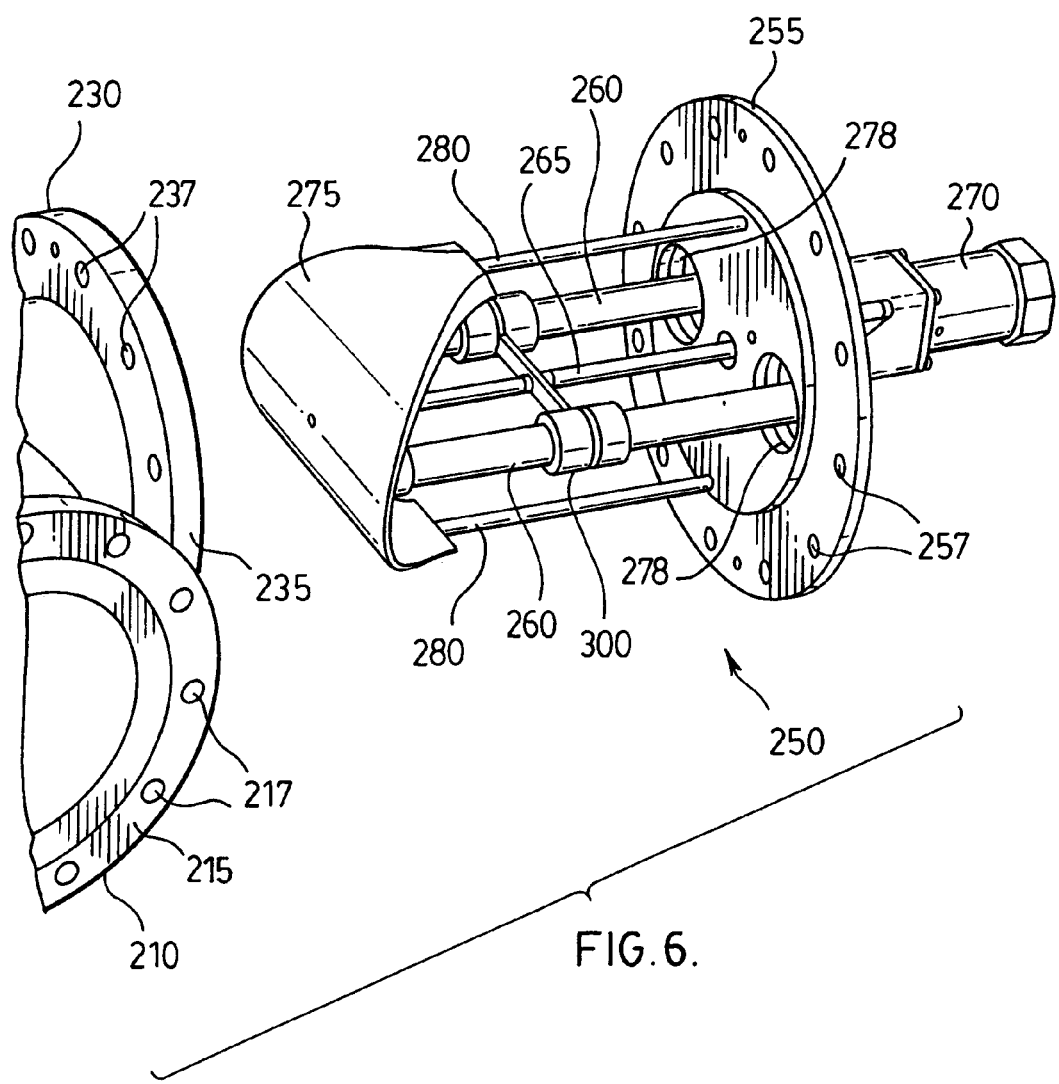

As illustrated, first flanged opening 210 and second flanged opening 220 are coaxially aligned along an axis parallel to the direction of fluid flow through fluid treatment system 200 as represented by arrow B (FIG. 4).

Fluid treatment system 200 further comprises an insertable radiation source module 250. Radiation source module 250 comprises a flange plate 255 having a series of connection openings 257 disposed therein. Radiation source module 250 further comprises a pair or radiation source assemblies 260 which are similar in construction with respect to radiation source assemblies 160 described above with reference to FIGS. 1 and 2. Radiation source module 250 further comprises a shaft 265 along which a cleaning device 300 may be moved back and forth. Disposed at the distal end of radiation source module 250 is a curved plate 275. Curved plate 275 comprises a pair of receptacles 262 which receive the distal end of each radiation source assembly 260. Curved plate 275 further comprises a receptacle 267 which receives the distal end of shaft 265. A pair of connection rods 280 serve to connect curved plate 275 to flange plate 255.

Radiation source module 250 further comprises a motor 270 for translating cleaning device 300 back and forth along shaft 265. Flange plate 255 comprises a pair of receptacles 278 which serve to receive cleaning device 300 when it is in the "parked" position.

Cleaning device 300 may be of the type described in Re. 36,896 referred to above. Thus, cleaning device 300 may comprise a cleaning chamber for receiving a cleaning fluid thereby relying on mechanical and chemical action to remove fouling materials from the exterior of radiation source assemblies 260. Alternatively, cleaning device 300 may be a so-called mechanical cleaning device relying on mechanical interaction only to remove fouling materials from the exterior of radiation source assemblies 260. A cellular material such as a sponge may be used in either version of the cleaning device—i.e. disposed in or integral with a cleaning chamber in the device described in Re. 36,896 or simply on its own relying on mechanical action.

Fluid treatment system 200 may be assembled in a manner similar to that described above for fluid treatment system 100 with reference to FIGS. 1 and 2. In this case, curved plate 275 has a shape which compliments the inside of ductile iron pipe fitting 205 or the like—this is best seen with reference to FIG. 3. The assembled device may then be installed in a manner similar to that described above with reference to fluid treatment system 100 and FIGS. 1 and 2.

The present fluid treatment system is particularly advantageous since the flanged pipe fitting to which is connected the radiation source module is made from ductile iron. Further, this allows for relatively simple retrofitting of the device into an existing fluid conveyance system. Still further, the treatment system is relatively easily serviceable and, for example, the radiation source modules can be taken off-line for servicing without the need to interrupt conveyance of fluid throughout the entire fluid conveyance system. That is the radiation lamps can be removed from the lamp sleeves without interrupting the flow of fluid through the reactor. Other advantages will be apparent to those of skill in the art having the present specification in hand.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. For example, it is possible to utilize bolted or non-bolted flanges in the ductile iron pipe fitting or the like of the present fluid treatment system. Further, it is possible to use a vanstone type flange or connect the fluid treatment unit using solvent welding. See the following Internet web site www.ipexinc.com/products/industrial.html or www.ipexinc.com/industrial/fittings.html—see page 23 for a description of a "vanstone" flange. Further to is possible to modify radiation source module 250 illustrated in FIGS. 3–6 to omit curved plate 275. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A fluid treatment system for placement in a flanged pipe fluid conveyance system, the fluid treatment system comprising:

a flanged ductile iron pipe fitting comprising:
 (a) a first flanged opening and a second flanged opening in substantial alignment to define a flow axis aligned substantially parallel to a direction of fluid flow through the first flanged opening and the second flanged opening;
 (b) a third flanged opening;
 (c) a removable radiation source module comprising a first flanged cover element configured to be removably coupled to said third flanged opening, the first flanged cover element having connected thereto at least two radiation source assemblies each comprising at least one elongate radiation source having a longitudinal axis substantially non-parallel to the flow axis; and
 (d) connecting structure configured to couple said first flanged cover element to said third flanged opening.

2. The fluid treatment system defined in claim 1, wherein the first cover element is in substantially fluid tight sealing engagement with a flange portion of the third flanged opening.

3. The fluid treatment system defined in claim 1, wherein the first cover element cover comprises a radiation source opening through which the radiation source may be removably inserted into the flanged ductile iron pipe fitting.

4. The fluid treatment system defined in claim 1, wherein the first cover element further comprises a first support for supporting a proximal end of the radiation source assembly.

5. The fluid treatment system defined in claim 4, wherein the radiation source assembly is cantilevered with respect to the first support.

6. The fluid treatment system defined in claim 1, wherein the flanged ductile iron pipe fitting further comprises a fourth flanged opening in substantial alignment with the third flanged opening to define a cross-flow axis substantially transverse to the flow axis.

7. The fluid treatment system defined in claim 6, wherein the fourth flanged opening comprises a second cover element.

8. The fluid treatment system defined in claim 7, wherein the second cover element is in substantially fluid tight sealing engagement with a flange portion of the fourth flanged opening.

9. The fluid treatment system defined in claim 7, wherein the second cover element further comprises a second support for supporting a distal end of the radiation source assembly.

10. The fluid treatment system defined in claim 9, wherein the second support comprises a receptacle for receiving the distal end of the radiation source assembly.

11. The fluid treatment system defined in claim 1, wherein the longitudinal axis of the radiation source is substantially orthogonal to the direction of the flow axis.

12. The fluid treatment system defined in claim 1, wherein the first cover element has connected thereto a plurality of radiation source assemblies.

13. The fluid treatment system defined in claim 1, further comprising a cleaning device for removing fouling materials from a surface of the radiation source assembly.

14. The fluid treatment system defined in claim 13, wherein the cleaning device comprises a cleaning sleeve in contact with an exterior surface of the radiation source assembly.

15. The fluid treatment system defined in claim 14, wherein the cleaning sleeve comprises a mechanical wiper.

16. The fluid treatment system defined in claim 15, wherein the mechanical wiper comprises an O-ring.

17. The fluid treatment system defined in claim 15, wherein the mechanical wiper comprises a mechanical brush.

18. The fluid treatment system defined in claim 15, wherein the mechanical wiper comprises a cellular material.

19. The fluid treatment system defined in claim 14, wherein the cleaning sleeve comprises a chamber for receiving a cleaning fluid.

20. The fluid treatment system defined in claim 19, wherein the chamber comprises a mechanical cleaning element.

21. The fluid treatment system defined in claim 20, wherein the mechanical cleaning element comprises a porous material.

22. The fluid treatment system defined in claim 20, wherein the mechanical cleaning element comprises a cellular material.

23. The fluid treatment system defined in claim 1, wherein the first flanged opening comprises a diameter in the range of from about 3 inches to about 64 inches.

24. The fluid treatment system defined in claim 1, wherein the second flanged opening comprises a diameter in the range of from about 3 inches to about 64 inches.

25. The fluid treatment system defined in claim 1, wherein the third flanged opening comprises a diameter in the range of from about 3 inches to about 64 inches.

26. The fluid treatment system defined in claim 1, wherein each of the first flanged opening, the second flanged opening and the third flanged opening comprises substantially the same diameter.

27. The fluid treatment system defined in claim 1, wherein: (i) the first flanged opening and the second flanged opening comprise substantially the same diameter, and (ii) the third flanged opening has a different diameter than the first flanged opening and the second flanged opening.

28. The fluid treatment system defined in claim 1, wherein the radiation source comprises an ultraviolet radiation source.

29. The fluid treatment system defined in claim 1, wherein the at least one radiation source assembly further comprises a protective sleeve surrounding the at least one elongate radiation source.

30. The fluid treatment system defined in claim 1, wherein the first cover element comprises a plurality of radiation source assemblies, each radiation source assembly comprising at least one elongate radiation source.

31. A method of installing a fluid treatment system in an existing piped fluid conveyance system, the method comprising the steps of:
 (a) extracting a section of pipe from the existing piped fluid conveyance system to define a flanged fluid intake and a flanged fluid feed;
 (b) disposing a flanged ductile iron pipe fitting between the flanged fluid intake and the flanged fluid feed, the flanged ductile iron pipe fitting comprising:
  (i) a first flanged opening and a second flanged opening in substantial alignment to define a flow axis aligned substantially parallel to a direction of fluid flow through the first opening and the second opening;
  (ii) a third flanged opening;
  (iii) a removable radiation source module comprising a first flanged cover element configured to be removably coupled to said third flanged opening, the first flanged cover element having connected thereto at least two radiation source assemblies each comprising at least one elongate radiation source having a longitudinal axis substantially non-parallel to the flow axis; and
  (iv) connecting structure configured to couple said first flanged cover element to said third flanged opening
 (c) connecting the first flanged opening to the flanged fluid intake in a substantially fluid tight manner; and
 (d) connecting the second flanged opening to the flanged fluid feed in a substantially fluid tight manner.

32. The method defined in claim 31, wherein the first cover element is in substantially fluid tight sealing engagement with a flange portion of the third flanged opening.

33. The method defined in claim 31, wherein the first cover element comprises a radiation source opening through which the radiation source may be removably inserted into the flanged ductile iron pipe fitting.

34. The method defined in claim 31, wherein the first cover element further comprises a first support for supporting a proximal end of the radiation source assembly.

35. The method defined in claim 34, wherein the radiation source assembly is cantilevered with respect to the first support.

36. The method defined in claim fluid treatment system defined in claim 31, wherein the flanged ductile iron pipe fitting further comprises a fourth flanged opening in substantial alignment with the third flanged opening to define a cross-flow axis substantially transverse to the flow axis.

37. The method defined in claim 36, wherein the fourth flanged opening comprises a second cover element.

38. The method defined in claim 37, wherein the second cover element is in substantially fluid tight sealing engagement with a flange portion of the fourth flanged opening.

39. The fluid treatment system defined in claim 37, wherein the second cover element further comprises a second support for supporting a distal end of the radiation source assembly.

40. The method defined in claim 39, wherein the second support comprises a receptacle for receiving the distal end of the radiation source assembly.

41. The method defined in claim 31, wherein the longitudinal axis of the radiation source is substantially orthogonal to the direction of the flow axis.

42. The method defined in claim 31, wherein the first cover element has connected thereto a plurality of radiation source assemblies.

43. The method defined in claim 31, further comprising a cleaning device for removing fouling materials from a surface of the radiation source assembly.

44. The method defined in claim 43, wherein the cleaning device comprises a cleaning sleeve in contact with an exterior surface of the radiation source assembly.

45. The method defined in claim 44, wherein the cleaning sleeve comprises a mechanical wiper.

46. The method defined in claim 45, wherein the mechanical wiper comprises an O-ring.

47. The method defined in claim 45, wherein the mechanical wiper comprises a mechanical brush.

48. The method defined in claim 45, wherein the mechanical wiper comprises a cellular material.

49. The method defined in claim 44, wherein the cleaning sleeve comprises a chamber for receiving a cleaning fluid.

50. The method defined in claim 49, wherein the chamber comprises a mechanical cleaning element.

51. The method defined in claim 50, wherein the mechanical cleaning element comprises a porous material.

52. The method defined in claim 50, wherein the mechanical cleaning element comprises a cellular material.

53. The method defined in claim 31, wherein the first flanged opening comprises a diameter in the range of from about 3 inches to about 64 inches.

54. The method defined in claim 31, wherein the second flanged opening comprises a diameter in the range of from about 3 inches to about 64 inches.

55. The method defined in claim 31, wherein the third flanged opening comprises a diameter in the range of from about 3 inches to about 64 inches.

56. The method defined in claim 31, wherein each of the first flanged opening, the second flanged opening and the third flanged opening comprises substantially the same diameter.

57. The method defined in claim 31, wherein the radiation source comprises an ultraviolet radiation source.

58. The method defined in claim 31, wherein the at least one radiation source assembly further comprises a protective sleeve surrounding the at least one elongate radiation source.

59. The method defined in claim 31, wherein the first cover element comprises a plurality of radiation source assemblies, each radiation source assembly comprising at least one elongate radiation source.

60. A fluid treatment system for placement in a flanged pipe fluid conveyance system, the fluid treatment system comprising:
- a flanged ductile iron pipe fitting comprising:
  - (a) a cylindrical ductile iron housing:
  - (b) a first flanged opening and a second flanged opening in substantial alignment to define a flow axis aligned substantially parallel to a direction of fluid flow through the first opening and the second opening;
  - (c) a third flanged opening;
  - (d) a removable radiation source module comprising a first cover element adapted to be removably coupled to said third flanged opening, the first cover element having connected thereto at least two elongate radiation sources each having a longitudinal axis substantially transverse to the flow axis, distal ends of said at least two elongate radiation sources being disposed within said cylindrical ductile iron housing.

61. The fluid treatment system defined in claim 60, wherein the first cover element is in substantially fluid tight sealing engagement with a flange portion of the third flanged opening.

62. The fluid treatment system defined in claim 60, wherein the first cover element cover comprises a radiation source opening through which the radiation source may be removably inserted into the flanged ductile iron pipe fitting.

63. The fluid treatment system defined in claim 60, wherein the first cover element further comprises a first support for supporting a proximal end of the radiation source assembly.

64. The fluid treatment system defined in claim 63, wherein the radiation source assembly is cantilevered with respect to the first support.

65. The fluid treatment system defined in claim 60, further comprising connecting structure configured to couple said first flanged cover element to said third flanged opening.

66. The fluid treatment system defined in claim 65, wherein said connecting structure comprises at least one bolt.

67. The fluid treatment system defined in claim 1, wherein said connecting structure comprises at least one bolt.

68. A water treatment radiation source module, comprising:
- a flanged cover plate configured to be removably coupled to a water pipe flanged opening, the water pipe having a direction of fluid flow;
- two radiation source modules cantilever-mounted to an inside surface of said flanged cover plate so that said radiation source modules and the flanged cover plate are configured to provide a radiation zone inside the water pipe, each radiation source module comprising a radiation source disposed inside of a protective sleeve, said radiation source modules being disposed non-parallel to said direction of fluid flow inside the water pipe;
- at least one connection aperture in said flanged cover plate and configured to provide electrical connection to said two radiation source modules; and
- connecting structure configured to couple said flanged cover plate to said water pipe flanged opening.

69. A water treatment radiation source module according to claim 68, further comprising:
- first and second cleaning devices, respectively configured to clean the two radiation source module protective sleeves;
- cleaning device support structure coupled to said first and second cleaning devices and configured to move the first and second cleaning devices along the two radiation source module protective sleeves, a portion of said cleaning device support structure being the cantilever-mounted to the inside surface of said flanged cover plate; and
- cleaning device drive structure coupled to an outside surface of the flanged cover plate and configured to drive said cleaning device support structure to cause the movement of the first and second cleaning devices along the two radiation source module protective sleeves.

70. A water treatment radiation source module according to claim 69, further comprising a cleaning device drive structure aperture in said flanged cover plate.

71. A water treatment radiation source module according to claim 68, wherein said a flanged cover plate comprises a round, ductile iron cover plate configured to be bolted to a standard water pipe flanged opening.

* * * * *